(12) United States Patent
Daniels et al.

(10) Patent No.: US 7,596,986 B2
(45) Date of Patent: Oct. 6, 2009

(54) METHOD OF TESTING LIQUID DROP IMPACT AND APPARATUS

(75) Inventors: Michael P. Daniels, Inver Grove Heights, MN (US); Ryan E. Marx, Rosemount, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 152 days.

(21) Appl. No.: 11/680,784

(22) Filed: Mar. 1, 2007

(65) Prior Publication Data

US 2008/0209981 A1 Sep. 4, 2008

(51) Int. Cl.
*G01N 3/30* (2006.01)
(52) U.S. Cl. ..................... 73/12.04; 73/12.01
(58) Field of Classification Search ..... 73/12.04–12.07, 73/12.09, 12.11, 12.13
See application file for complete search history.

(56) References Cited

U.S. PATENT DOCUMENTS

| | | | | |
|---|---|---|---|---|
| 4,265,107 A | * | 5/1981 | Cheng et al. | 73/28.05 |
| 4,531,400 A | * | 7/1985 | Nevel | 73/12.13 |
| 5,714,675 A | * | 2/1998 | Yoshida et al. | 73/12.04 |
| 6,045,728 A | * | 4/2000 | Chen et al. | 264/1.21 |
| 6,171,704 B1 | * | 1/2001 | Mosser et al. | 428/450 |
| 6,536,258 B1 | * | 3/2003 | Mostaghel | 73/12.01 |
| 7,219,568 B2 | * | 5/2007 | Folestad et al. | 73/864.81 |

OTHER PUBLICATIONS

Weiss, Daniel A. Yarin, Alexander L, Single Drop Impact one Liquid Films, 1999, Faculty if Mechanical Engineering, Journal of Fluid Mechanics, 229-254.*
Davis, Robert H., Rager, Dean A., Good, Brian T., Kantak, Advait, 2002, Department of Chemical Engineering, University of Colorodo, NASA Conference Publication, 48-62.*
Adler, "Rain Impact Retrospective and Vision for the Future"; WEAR 233-235 (1999) 25-38; Elsevier Science.
Adler et al., Multiple Simulated Waterdrop Impact Damage in Zinc Sulfide at Supersonic Velocities, SPIE vol. 1760, Window and Dome Technologies and Materials 111 (1992) pp. 303-315.
Engneering Laboratories Inc., Your Single Source of Plastic Balls, 2004-2005, www.plasticballs.com, printed from web on Jan. 25, 2007.

* cited by examiner

*Primary Examiner*—Lisa M Caputo
*Assistant Examiner*—Freddie Kirkland, III
(74) *Attorney, Agent, or Firm*—Sandra K. Nowak

(57) ABSTRACT

Methods and apparatus of evaluating liquid impact are described that included providing a thin layer of an (e.g. atmospheric) liquid, such as water, on the surface of the test sample while being impacted with a (e.g. polymeric) pellet.

16 Claims, 3 Drawing Sheets

METHOD OF TESTING LIQUID DROP IMPACT AND APPARATUS

BACKGROUND

Rain impact and rain erosion testing is important for evaluating aerospace components and materials. Many companies do not have internal test equipment to evaluate the resistance of their products to rain impact or erosion. Various products and materials can be submitted for testing by the University of Dayton Research Institute, located at Wright-Patterson Air Force Base. This facility uses a rotating arm device such as described in greater detail in William F. Adler, "Rain Impact Retrospective and Vision for the Future"; Wear 233-235, 1999, pp. 25-38. This test has become a standard in the industry for qualifying aerospace components and materials.

Rocket sleds are another device that has been used to evaluate water drop impacts. A rocket sled propels an array of test specimens through an extended sprinkler system, approximating on the ground what takes place in the atmosphere.

In addition, both ice and liquid water drop collisions have been evaluated in the GRCI Hydrometeor Impact Facility. A test specimen is mounted at the front end of a sabot which is propelled down the range by a small charge of gunpowder. The specimen impacts a single falling water drop.

W. F. Adler, J. W. Flavin, and J. P. Richards, "Multiple Simulated Waterdrop Impact Damage in Zinc Sulfide at Supersonic Velocities", SPIE Vol. 1760, Window and Dome Technologies and Material III, 1992, pp. 303-315 describes that nylon bead impacts provide a good simulation of water drop impact damage on zinc sulfide for a wide range of impact conditions.

SUMMARY

The Applicant has found that the rotating arm device has the disadvantage of the water droplets impacting the test sample surface in a random manner. Accordingly, some portions of the test sample are impacted with many more droplets than other. This can create a substantial amount of variability in the test results.

The Applicant has found that methods of evaluating liquid impact can be improved by providing a thin layer of an (e.g. atmospheric) liquid, such as water, on the surface of the test sample while being impacted with a (e.g. polymeric) pellet. This method can have the advantage of reduced variability since the location and number of impacts can be precisely controlled. The inclusion of a thin layer of liquid causes the impacts to more closely simulate fluid droplet impacts. In the absence of liquid, one cannot predict failures that may be caused by the liquid being forced into a (e.g. laminated or composite) test sample.

In some embodiments, methods of evaluating liquid impact or erosion are described. In one aspect, the method comprises providing a test sample, providing a film of (e.g. atmospheric) fluid on a surface of the sample; impacting the surface with at least one pellet; and measuring at least one physical property of the test sample after impact.

In another embodiment, an apparatus for evaluating liquid impact or erosion is described comprising a means for fixing a test sample; a means for providing a film of liquid on a surface of the sample; and a means for impacting the surface with pellets.

DETAILED DESCRIPTION OF THE PREFERRED EMBODIMENTS

Presently described are methods and apparatus suitable for simulating the impact of a liquid drop, such as water drops impacting a surface of an aircraft traveling at subsonic to supersonic speeds.

The method generally comprises impacting a target surface, such as the surface of a test sample, with pellets. The target surface includes a thin layer of liquid such as water.

The apparatus for impacting the pellet surface typically comprises shooting a pellet onto a target surface. The impacting pellet transfers its energy of motion to the fluid layer on impact and then to the target surface of the test sample via the pressure waves created in the fluid layer.

In one embodiment, an apparatus for evaluating liquid impact or erosion is described that generally comprises a means for providing a film of liquid on a surface of the sample and a means for impacting the surface with pellets. In some aspects, the apparatus may also include a means for fixing a test sample. Alternatively or in addition thereto, the apparatus may also comprise a means for measuring the velocity of each pellet prior to impacting the test sample as well as recording the number of impacts.

Although other means for impacting the surface of the test sample with pellets could be employed, one means is based on air guns technology used to propel (e.g. polymer) pellets at a desired velocity. For testing aerospace materials, the velocity typically ranges from 200 mph to 5000 mph. Various air guns are conveniently commercially available from various manufacturers such as Crossman, Daisy Outdoor, Remington, etc. The durability of other materials may be tested at lower velocities, ranging for example from 5 mph to 200 mph.

In one simple assembly of a suitable apparatus (not shown), the test sample is fixed in a substantially horizontal position such as by taping the test sample to a bench top. An air gun is mounted above the test sample such that the muzzle of the gun is a suitable distance from the test sample. A reservoir is provided on the surface of the test sample such as by bonding a gasket of suitable thickness. This reservoir can be filled with liquid to a desired amount in order to provide a suitable film of liquid on the surface of the test sample.

Figure 1:
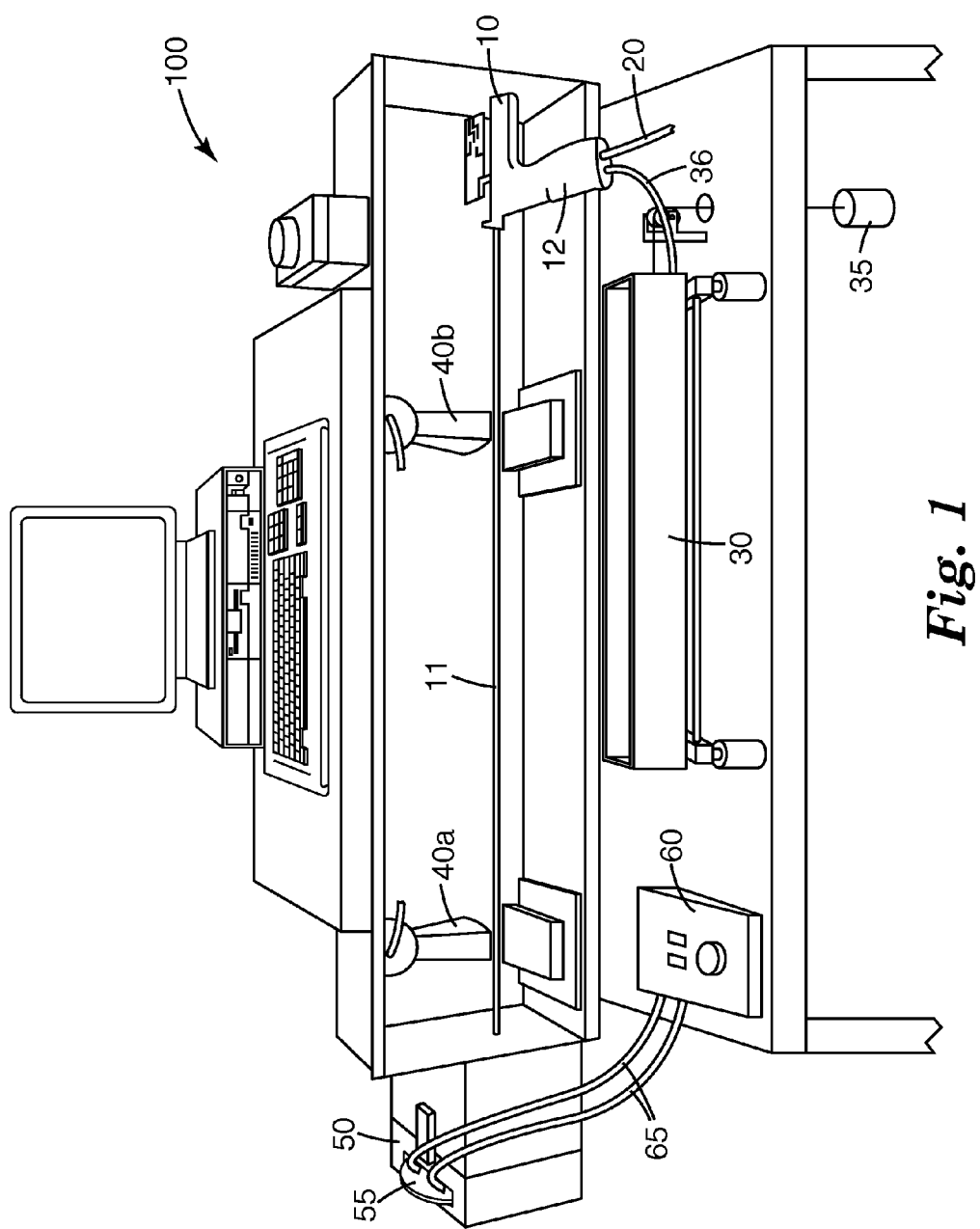
FIG. 1 is a schematic view of an illustrative apparatus of the invention.

A schematic view of another embodied testing apparatus 100 is depicted in FIG. 1. This device also employs an air gun 10 connected to a compressed (e.g. nitrogen) gas cylinder (not shown) via a ¼ inch diameter stainless steel hose 20. The nitrogen is used to provide pressure to propel one or more pellets from the gun to impact the test specimen.

Figure 2:
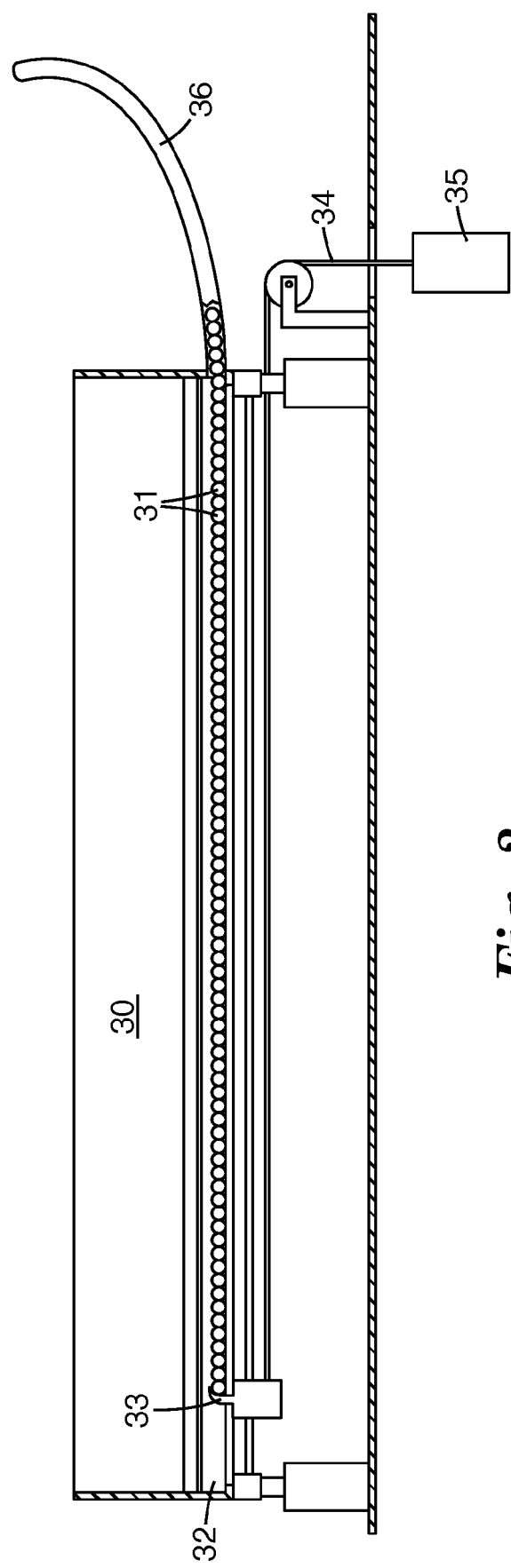
FIG. 2 is a cross-sectional view of the hopper of the apparatus of FIG. 1.

Various means can be used to provide the pellets to the air gun. With reference to FIGS. 1 and 2, the pellets 31 may be fed to the gun via a hopper 30 that allows for continuous feeding for the pellets. The hopper as shown in FIGS. 1 and 2 consists of a (50.8 cm long by 5.7 cm wide by 3.8 cm deep) container with a V-shaped bottom ending in a channel 32 for dispensing pellets to the gun. When the channel is closed, the width of the channel has an opening smaller than the diameter of the pellet (e.g. 3.2 mm). When the channel is open, the channel has an opening slightly larger than the diameter of a single pellet (e.g. 4.8 mm) yet narrower than the diameter of two pellets to allow a single row of pellets to enter the channel. The channel is designed such that when closed, the pellets within the channel are pushed with a (e.g. stainless steel) finger 33 freely, single file, toward the gun while preventing other pellets from entering the channel. The row of pellets can be advanced forward toward the front of the hopper by attaching to cable 34 that is tensioned with a (e.g. 2 pound) hanging weight. The 2 pound weight is used to advance the pellets up the feeding tube into the magazine 12 which feeds the gun. This weight provides sufficient force to advance the pellets up the tube, but not excessive force such that the pellets bypass the propulsion site. When the finger reaches the end of the hopper and there are no longer pellets in the channel, a gear driven motor can pull back the finger to the end of the hopper. The channel can then be opened and refilled with a row of pellets as previously described.

Alternatively, a gravity fed hopper may be positioned above the air gun. To improve the free flowing movement of the pellets, it may be desirably to treat the surface of the pellets with an antistatic agent or friction reducing additive such as talc.

With reference to FIG. 1, the apparatus may optionally include a chronograph to measure and record the velocity of the pellet. A suitable chronograph is commercially available from Competitive Edge Dynamics, Orefield, Pa., under the trade designation CED Millenium. A typical arrangement includes the two sensors 40a and 40b positioned a suitable distance apart (e.g. 2 feet) that includes optical sensors for sensing the passing of the pellet through a substantially transparent barrel 11. In one embodiment, the pellet leaves the gun and travels less than about 2 inches before impacting the test sample. Such close spacing typically prevents velocity measurements but increases accuracy of the precise location the pellet impacts the test sample surface.

The test sample(s) can be mounted within a (10.2 cm long by 13.3 cm wide by 17.8 cm tall) chamber 50 that contains the muzzle of the gun. A single test sample can be mounted within the chamber or more than one test sample can be mounted on a single disc 55. In some aspects, the test sample is stationary during impact. In other aspects, the test sample may be moving during impact. For example, the disc 55 may continuously revolve in combination with (e.g. synchronized) firing of pellets by the gun. Alternatively, disc 55 may revolve to a fixed position between pellet impacts. The test sample is preferably mounted at an angle (e.g. of about 85 degrees relative to the path of the pellet). This ensures that the pellet will not be deflected back into the path of a subsequent pellet and allows the pellet to fall into a collection receptacle.

When the test sample is fixed in a substantially vertical position such as depicted in FIG. 1, it is preferred that a (e.g. re-circulating) pump 60 is used to deliver a continuous film of (e.g. water) liquid to the surface of the test sample. A (e.g. ¼ inch diameter polyethylene) tube 65 extends from the pump to the surface of the test sample. The end of the tube that delivers water to the test specimen is preferably cut at an angle such that when the tube is pressed against the test specimen, a sheet or film of water covers the test sample. Other liquid delivery devices may also be employed.

The force of the impacting pellet (i.e. traveling at velocities ranging from 200 mph to 5000 mph) in combination with the liquid layer on the surface of the test sample is believed to create a pressure that is at least as high as water hammer pressure. In contrast, power washing for example produces about 1/10 of such pressure created by the impacting pellet.

The apparatus and method described herein could be used to measure the effects of impact and/or erosion for a variety of purposes. The apparatus and method is well-suited for testing components and materials for use in the aerospace industry, particularly those components and materials that are exposed to the outdoor environment of the exterior or such aircraft or spacecraft. Typical components and materials that may be employed as the test sample include for example protective tapes, sprayable coatings, as well as metals and composite material.

In many instances, water is the fluid of greatest interest. However, the atmosphere of other planets is known to contain different gases such as methane, ethane, or propane, which can condense to liquid droplets when contacting a spacecraft traveling at high speeds. Accordingly, various (e.g. hydrocarbon-based) organic liquid may also be used.

The liquid is provided on the surface of the test sample at a suitable thickness such that a substantially continuous sheet of film of liquid is present on the impacted surface of the test sample. The thickness of the liquid may vary. However, in general the thickness of the liquid layer is sufficiently low such that shock waves created in the liquid layer are transferred to the test sample surface. Typically, the thickness of the liquid is at least 0.001 inches and typically no greater than 0.10 inches. When the liquid exhibits a high surface tension on the surface of the test sample, such as the case when water is placed on a polymeric surface, it may be desirable to add a suitable surfactant to reduce the surface tension of the liquid.

The method and apparatus is also surmised to be adaptable to the testing of other components and materials that are subject to exposure to the outdoor environment such as building materials including siding materials (e.g. wood, cement board, vinyl, and aluminum), doors, windows, roofing shingles, decking, paint, varnish, as well as various waterproofing and sealant materials; retroreflective traffic signs and other types of (e.g. non-reflective) signs; pavement markings and pavement marking tapes.

In some aspects, the test sample may simply be visually examined for wear or damage such as cracking, pitting, delamination, or adhesion failure before and after impact. Alternatively one or more product performance tests can conducted prior to and after pellet impact of the test sample surface. Representative tests includes may include for example, gloss, color shift, adhesion (cross hatch and peel strength), abrasion resistance, tensile and elongation, retroreflectance, haze, chemical changes detected by a range of analytical techniques (IR, UV/Visible spectrometry, etc.), as well as any loss of intended function.

The pellet may have any suitable shape, provided the shape is amenable to being propelled at the target at a reproducible velocity. Commercially available pellets for use in air gun are typically substantially spherical or substantially cylindrical wherein the surface that impacts the target generally has a conical shape.

In order to be propelled at the test sample with an air gun, the pellets are generally relatively small, having a diameter of at least about 1 mm and typically no greater than about 10 mm. The diameter is typically about 2 mm, about 3 mm, about 4 mm, about 5 mm, or about 6 mm.

The pellet may be comprised of a variety of materials such as ice, a gel, as well as various thermoplastic or thermosetting polymeric materials. Polymeric pellets have been formed from various thermoplastic materials such as acrylic, cellulose acetate, nylon, polyolefins (e.g. polypropylene, high and low density polyethylene), PVC, Teflon, polystyrene, polycarbonate, and polyurethane. Thermoplastic pellets are surmised to be preferred in view of their wide availability and ability to form such material into a desired shape. Polymeric pellets are conveniently commercially available from a variety of manufactures. One source of (i.e. plastic ball) polymeric pellets is http://www.plastic balls.com.

It is surmised desirable that the density of the pellet impacting the test surface is similar in density to that of the film of liquid on the surface of the test sample. For example, if the density of the liquid is X, the pellet typically has a density ranging from 0.5X to 1.5X. Typically solid pellets are more readily available and easy to fabricate. The density of various solid thermoplastic pellets is most typically about 0.90 g/cc to about 1.50 g/cc. However, hollow pellets and pellets formed from foamed polymeric materials could alternatively use when a lower density pellet is desired.

Although selecting a pellet having a density similar to that of the liquid provided on the test sample surface is believed to be important for aerospace testing purpose, other types of pellets could be used for different test purposes. For example, if one wanted to test erosion of a pavement marking caused by salt or gravel, it may be suitable to use employ a salt solution on the test sample surface and impact the test surface with an inorganic particulate containing pellet.

The pressure developed under the pellet and transferred through the liquid layer depends on the shape of the pellet. A substantially spherical pellet will produce a pressure profile with the highest pressure at the center of the impact zone between the pellet and fluid, and decreasing to the edges of the impact zone. Alternatively, a pellet having a conical-shaped impacting surface will produce the highest pressure at the tip of the cone. However, the impact of a water drop with a surface, traveling at the speeds described above, produces a slightly higher pressure on the circular edges of the initial contact region of the drop with the target. This means that the pressure profile starts a little higher on the edges and is almost flat through the center of the contact region.

Although a substantially spherical pellet may not be the "perfect shape" for simulating water drop impact, spherical pellets are suitable for use in the method and apparatus described herein. It is surmised however, that the shape of the (e.g. polymeric) pellet can be changed such that as it collides with the (e.g. water) liquid layer surface it will produce a pressure profile in the liquid layer nearly equal to that seen from a drop of water colliding with the same. It is surmised that the surface of the pellet that contact the liquid may be concave or substantially flat rather than convex.

The shape of the impacting face including its impacting cross sectional shape, the length of the projectile, the type of material the projectile is made from, and velocity can all be adjusted to provide any pressure profile. This provides an easy means of duplicating natural rain impacts. It also provides a means of studying, in a controlled and deliberate fashion, impact profiles expected from deformed raindrops or that have larger or smaller radii.

EXAMPLE 1

A suitable apparatus was assembled using an air gun available under the trade designation "Remington AirMaster 77". This is a pump BB gun that can shoot 4.5 mm BB's at ~750 fps. The gun was mounted (clamps) in a lab hood vertically with the muzzle pointing toward the bottom of the hood. Since the literature describes the use of PMMA plates to demonstrate many of the physical principles of liquid drop collisions at moderate to high velocity, ¼ inch thick Plexiglas (PMMA) plates were taped to the bottom of the hood beneath the muzzle to use as targets. In order to approximate collisions with raindrops at a speed of about 500 mph (750 fps=511 mph), the gun was pumped 10 times to deliver the BB's at a velocity of ~750 fps velocities. The actual velocity is surmised to be slightly higher since nylon BB's were used rather than the steel BB's normally used with this gun.

Tape was used to build reservoir walls having an area of about 1 cm×4 cm and a depth of about 0.025 to 0.09 inches. A solution of 250 mL of tap water and surfactant (13 drops of Joy Ultra dish washing liquid) was prepared. By reducing the surface tension of the water with the surfactant the solution could wet out the reservoir completely allowing for accurate calculation of the thickness of a given volume within the reservoir. Experiments were conducted using the following volumes and corresponding thicknesses of water solution.

| Volume | Film Thickness of Water (1$^{st}$ Set) | Film Thickness of Water (2nd Set) |
| --- | --- | --- |
| 0.05 mL | 0.005 inches | 0.0052 inches |
| 0.1 mL | 0.01 inches | Not tested |
| 0.15 mL | Not tested | 0.0155 inches |
| 0.2 mL | 0.02 inches | 0.0207 inches |
| 0.25 mL | 0.025 inches | 0.0259 inches |
| 0.3 mL | 0.03 inches | 0.0311 inches |
| 0.4 mL | Not Tested | 0.0414 inches |

In the first set of experiments, the distance between the gun muzzle and the PMMA target three inches. There was little difference in damage of the PMMA plates regardless of the water thicknesses because the escaping air preceded the nylon bead and pushed some of the water out of the way prior to collision.

In the second set of experiments, the gun was moved to about 1 foot above the PMMA target plates. A slightly smaller reservoir area (1 cm×3.8 cm) was used resulting in higher thickness for the same volume as reported in the above table.

When the water thickness was 0.0259 inches and greater, the damage to the PMMA plate was less obvious damage. More damage, yet similar in extent was observed for water thicknesses of 0.0052 to 0.0207 inches.

The testing apparatus of FIG. 1 was assembled as previously described using the following components.

| Component (FIG. 1 reference numeral) | Supplier, Location | Trade Designation |
| --- | --- | --- |
| .177 caliber air gun (10) | European American Armory Corporation, Cocoa, FL, | "Drozd Air Gun". |
| ¼ inch diameter stainless steel hose (20) | Swagelok Company, Solon, OH | |
| Compressed nitrogen | Oxygen Service Company, St. Paul, MN | |
| 4.5 mm Grade II acetate pellets | Engineering Laboratories, Inc, Oakland, NJ | |
| Pump (60) | VWR, West Chester, PA | Part No. 23609-170 |

EXAMPLES 2 AND 3 AND COMPARATIVE EXAMPLES C1 AND C2

Four test samples were prepared by die cutting 6.1 cm diameter circular samples with 2.2 cm diameter hole in the middle. Two samples were cut from 3M™ Polyurethane Protective Tape 8667 HS ("8667"; black tape with a polyurethane thickness of 0.025 inches and an adhesive thickness of 0.003 inches) and two samples were cut from 3M™ Polyurethane Protective Tape 8681 HS ("8681"; gray tape with a polyurethane thickness of 0.012 inches and an adhesive thickness of 0.002 inches), both commercially available from 3M Company, St Paul, Minn.

The sample holder was cleaned by spraying it with isopropanol and rubbing it dry with a paper towel. The test sample was then adhered to the surface of a sample holder (disk of 304 stainless steel having an outer diameter of 7.6 cm and a central hole with a diameter of 0.35 cm) using hand pressure to create a good bond between the adhesive of the tape and the test substrate. The test sample was allowed to dwell on the sample holder for 24 hours at approximately 23.9° C. and 50% relative humidity prior to impact testing. The sample holder had six additional holes located equidistantly around the circular test substrate and 0.2 cm from the outer edge. Each of the six holes had a diameter of 0.15 cm. The six holes are in alignment with pins on the chamber that prevent the test sample from moving or rotating during impact testing.

The test specimen of Examples 2 and 3 and Comparative Examples C1 and C2 on the sample holder was independently inserted into the sample chamber door and the door was closed and latched. Comparative Examples C1 and C2 were tested dry, i.e., without water; Examples 1 and 2 were tested wet, i.e., with water application to the surface of the test specimen at a rate of about 600 ml/min via a chemical transfer pump commercially available as Part No. 23609-170. The water pump tube was pressed against the top of the test specimen and the water pump was turned on. This created an approximately 1 mm thick water film that covered the surface of the test specimen.

The pellets used to impact the test specimens were 4.5 mm diameter Grade II acetate pellets. The pressure used to propel the pellets was supplied via a nitrogen cylinder set to 90 psi. The test specimens were impacted at a rate of 4 shots per second.

The test specimen was visually inspected intermittently for damage and two types of damage were recorded. The first was "Shots to Damage", i.e., the number of shots needed to create a damage site. This was observed as a pinhole through the surface of the test specimen, but with no substrate visible. The second was "Shots to Failure", i.e., the number of shots needed for the sample to show complete failure. This was observed as the sample eroding through the test specimen such that the substrate was visible.

For Example 2 and Comparative Example C1 six different sites on the test specimen were tested and the average recorded in Table 1. For Example 3 and Comparative Examples C2 five different sites on the test specimen were tested and the average recorded in Table 1

TABLE 1

| Example | Test Specimen | Test Condition (Wet or Dry) | Shots to Damage (Average) | Shots to Failure (Average) |
|---|---|---|---|---|
| C1 | 8667 | Dry | 11.7 | 170.0 |
| 2 | 8667 | Wet | 71.7 | 676.7 |
| C2 | 8681 | Dry | 1.4 | 10.4 |
| 3 | 8681 | Wet | 8.4 | 63.4 |

The data in Table 1 show a dramatic increase in both "Shots to Damage" and "Shots to Failure" when impact testing was done with application of water to the surface of the test specimen during testing compared to specimen testing without application of water.

Figure 3:
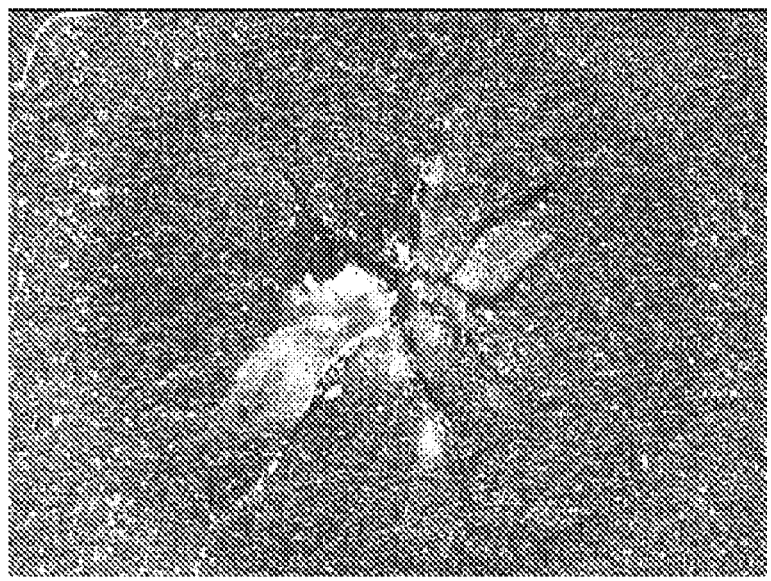
FIG. 3 illustrates the surface of a test sample after impacting the test surface with pellets when a thin layer of water is provided on the test sample surface.
Figure 4:
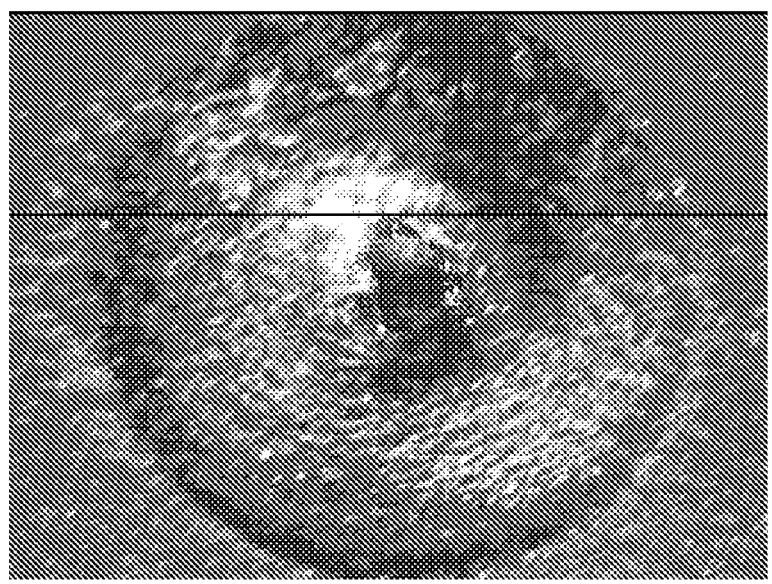
FIG. 4 illustrates the surface of a test sample after impacting the test surface with pellets without a thin layer of water is provided on the test sample surface.

FIGS. 3 and 4 illustrate the surfaces of Example 2 and Comparative Example C1 respectively as observed under a microscope at a magnification of 2.5× after the surface were impacted by the pellets. It is apparent from these illustrations that the inclusion of the thin layer of (e.g. water) liquid on the surface of the test sample also resulted in different damage characteristics. In FIG. 4, the surface of the test sample was indented by the impacting pellets leaving a pit in the central region of the test sample. However, in FIG. 3 with the inclusion of water on the test sample surface, the impacted area exhibited fractures. Such fracturing was not evident in FIG. 4.

What is claimed is:

1. A method of evaluating liquid impact or erosion comprising:
   providing a test sample;
   providing a film of liquid on a surface of the test sample wherein the liquid comprises a surfactant suitable for reducing the surface tension of the liquid;
   impacting the film of liquid with at least one pellet wherein the pellet impacts the test sample surface at a velocity ranging from 200 mph to 5000 mph;
   measuring at least one physical property of the test sample after impact.

2. The method of claim 1 wherein the pellet has a maximum dimension ranging in size from about 1 mm to about 10 mm.

3. The method of claim 1 wherein the film of liquid has a thickness ranging from about 0.001 inches to 0.050 inches.

4. The method of claim 1 wherein the pellet has a density of about 0.90 to 1.50 g/cc.

5. The method of claim 1 wherein the liquid comprises water.

6. The method of claim 1 wherein the pellet comprises a polymeric material.

7. The method of claim 1 wherein the pellet is substantially spherical.

8. The method of claim 1 wherein the liquid is an organic material.

9. The method of claim 1 wherein the test sample is a product or material for use as an exterior component of an aerospace vehicle.

10. The method of claim 1 wherein the physical property is visible surface damage.

11. The method of claim 1 wherein the test sample is stationary during impact.

12. The method of claim 1 wherein the test sample is moving during impact.

13. An apparatus for evaluating liquid impact or erosion comprising:
    a means for fixing two or more test samples on a rotating wheel;
    a means for providing a film of liquid on a surface of the sample, the liquid including a surfactant suitable for reducing the surface tension of the liquid; and a means for impacting the surface with a pellet at a velocity ranging from 200 mph to 5000 mph.

14. The apparatus of claim 13 wherein the test samples are fixed in a substantially horizontal position and the film of liquid is contained in a reservoir bonded to the surface of the sample.

15. The apparatus of claim 13 wherein the test samples are fixed substantially vertically and a substantially continuous film of liquid is delivered onto the sample surface.

16. The apparatus of claim 13 wherein an air gun is employed to shoot the surface with polymeric pellets.

* * * * *